United States Patent
Sato et al.

(10) Patent No.: US 7,329,369 B2
(45) Date of Patent: Feb. 12, 2008

(54) SEMICONDUCTOR NANOPARTICLE SURFACE MODIFICATION METHOD

(75) Inventors: Keiichi Sato, Tokyo (JP); Shinya Hattori, Tokyo (JP); Taeko Chiba, Tokyo (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 256 days.

(21) Appl. No.: 11/325,533

(22) Filed: Jan. 5, 2006

(65) Prior Publication Data

US 2006/0145138 A1    Jul. 6, 2006

(30) Foreign Application Priority Data

Jan. 6, 2005    (JP)    ............................. 2005-001583

(51) Int. Cl.
C09K 11/02    (2006.01)
C09K 11/08    (2006.01)

(52) U.S. Cl. .................. 252/301.36; 977/773; 977/902

(58) Field of Classification Search .......... 252/301.36; 977/773, 902

See application file for complete search history.

(56) References Cited

U.S. PATENT DOCUMENTS

2003/0194731 A1    10/2003    Sato et al.

FOREIGN PATENT DOCUMENTS

EP        1 333 280 A1        1/2003
WO    WO 02/055186 A2    10/2001

*Primary Examiner*—Evan Pert
(74) *Attorney, Agent, or Firm*—Reed Smith LLP; Stanley P. Fisher, Esq.; Juan Carlos A. Marquez, Esq.

(57) ABSTRACT

Semiconductor nanoparticles having high luminescence properties that are preferable for applications and uses of biotechnology are provided.

With the use of electric charges on the surfaces of particles, the particles and selected polymers are allowed to electrostatically bind to each other, such that the surfaces of the particles are coated. The polymers are allowed to crosslink to each other, resulting in the improved durability of the particles. Further, functional groups contained in the polymers are exposed on the surfaces of the particles. Accordingly, semiconductor nanoparticles that are preferably utilized for applications such as staining and labeling of biopolymers have been synthesized.

25 Claims, 6 Drawing Sheets

After coating

Before coating

SEMICONDUCTOR NANOPARTICLE SURFACE MODIFICATION METHOD

BACKGROUND OF THE INVENTION

1. Field of the Invention

The present invention relates to a semiconductor nanoparticle having high luminescence properties and a method for synthesizing the same. Moreover, the present invention relates to a fluorescent reagent and an optical device comprising such semiconductor nanoparticle.

2. Background Art

Semiconductor nanoparticles with particle sizes of 10 nm or less are located in the transition region between bulk semiconductor crystals and molecules, so that they exhibit physicochemical properties different from those of either bulk semiconductor crystals or molecules. In such region, the degeneracy of energy bands that is observed in bulk semiconductors is removed and the orbits become discrete, so that a quantum size effect appears in which the energy width of the forbidden band changes depending on particle size. According to the appearance of the quantum size effect, the energy width of the forbidden band of a semiconductor nanoparticle decreases or increases in response to an increase or decrease of particle size. This change of the energy width of the forbidden band affects the fluorescence properties of the particle in question. A particle that has a smaller particle size and wider forbidden band energy width tends to have a shorter a fluorescent wavelength, while a particle that has a larger particle size and a narrower forbidden band energy width tends to have a longer fluorescent wavelength. That is, it is possible to create a desired fluorescent color by controlling particle size. In addition to the properties described above, semiconductor nanoparticles have high durability against excitation lights, etc., and a region which can be excited widely extends more towards the shorter wavelengths than the fluorescent wavelength, so that simultaneous excitation of multiple fluorescent colors is also possible by using a single excitation light source. Thus, semiconductor nanoparticles serving as fluorescent material are gaining significant attention. Specifically, the fields related to biotechnology and to optical device technology are listed as fields in which semiconductor nanoparticles have been used actively, and further applications are expected in the future.

In order to use semiconductor nanoparticles serving as fluorescence material, it is desired that such particles have fluorescence properties in which the fluorescence spectrum has a waveform with a narrow and sharp full width half maximum (FWHM). Thus, it is necessary that the band gap fluorescence properties in response to the forbidden band widths of the semiconductor nanoparticles are made effective. However, even if a prepared bulk particle has a monodisperse particle size, such particle per se does not exhibit sufficient band gap fluorescence properties. As a reason for this, the presence of the energy level existing mainly at the surface site of the semiconductor nanoparticle is mentioned, and, since the energy level exists in the forbidden band inside the particle, it has been thought that the band gap fluorescence properties are inhibited. Due to the reasons mentioned above, the inactivation of the aforementioned energy level and the obtaining of the band gap fluorescence have become significant subjects.

A method for providing a solution to this subject relates to a (CdSe)ZnS nanoparticle, which has a so-called core-shell type structure. The aforementioned method involves obtaining high luminescence properties by coating the semiconductor nanoparticle (CdSe) with a second semiconductor material (ZnS), which has a wider forbidden band width than that of the particle, and removing the energy level in the forbidden band of the particle, thereby making the band gap fluorescence properties effective. (JP Patent Publication (Kohyo) No. 2001-523758 A and J. Phys. Chem. B. 101: 9463 (1997))

In addition, by achieving particle size monodispersion in an aqueous solution and carrying out particle surface reforming, inventors have been studying a method for making band gap fluorescence effective. As a result of intensive studies carried out by the inventors, a method for obtaining semiconductor particles having commercially adequate fluorescence properties has been developed, in which semiconductor nanoparticles synthesized by a size-selective photo-etching technique are treated in a refining process, the particles are subjected to surface reforming using sodium hydroxide or amine-ammonium compounds, and the energy levels at the particle surfaces are made inactive by arranging the electron-releasing groups on the surfaces, such that the band gap fluorescence properties are made effective. Moreover, by coating the obtained nanoparticles with organic compounds such as one composed of amphiphilic molecules, we succeeded in obtaining semiconductor nanoparticles having improved chemical durability. According to a series of these methods, synthesis of semiconductor nanoparticles that have high luminescence properties was realized by using a safe and simple technique in an aqueous solution. The nanoparticles per se have sufficient durability. In addition, high durability can be imparted to them by allowing preferably usable organic compounds, such as amphipathic molecules, to bind to each other. However, for the purpose of synthesizing high-functional semiconductor nanoparticles by a more convenient method, the inventors have arrived at the present invention.

SUMMARY OF THE INVENTION

The inventors have invented a surface treatment, such as an OH coating or ammonia treatment, as a surface reforming technique for semiconductor nanoparticles. However, semiconductor nanoparticles that have been subjected to a surface treatment, such as an OH coating or ammonia treatment, do not have sufficient durability against external factors, typically including pH. It has been an objective to solve the aforementioned problems.

In order to protect semiconductor nanoparticles from the aforementioned external factors, the inventors have attempted a method of coating obtained nanoparticles with organic material. Further, the inventors have conducted studies of semiconductor nanoparticles having chemical durability and showing high luminescence properties. When semiconductor nanoparticles are utilized for bio-related applications, it is preferable to modify the surfaces of such semiconductor nanoparticles with a functional group such as a carboxyl group. Also, it is necessary to modify semiconductor nanoparticles so as to improve the industrial availability thereof.

The inventors found that semiconductor nanoparticles exerting high luminescence properties can be obtained by applying surface reforming to semiconductor nanoparticles, and modifying the semiconductor nanoparticles with a functional group-containing polymer, thereby allowing the polymer to form a crosslink via a crosslinking agent.

That is, firstly, the present invention is an invention of a semiconductor nanoparticle exerting high luminescence properties, which is modified with a functional group-containing polymer that electrostatically binds to the surface of the semiconductor nanoparticle. The modifying groups of the functional group-containing polymer form a crosslinking bond via a crosslinking agent.

Preferably, specific examples of functional groups of the functional group-containing polymer include, but are not limited to, one or more functional groups selected from the group consisting of —COOH, —OH, —$NH_2$, —SH, —OCN, —CNO, —CHO, —CH=O, —CH=$CH_2$, and —C≡CH, so that various types of crosslinking reactions can be involved.

The functional group-containing polymer may directly bind to the surface of a semiconductor nanoparticle or bind thereto via a semiconductor nanoparticle-coating compound.

Preferably, specific examples of the crosslinking bond include one or more bonds selected from the group consisting of an ester bond, an amide bond, an imide bond, an ether bond, a urethane bond, a sulfide bond, a polysulfide bond, a carbonate bond, a thiol bond, a thioester bond, and a thiourethane bond. The crosslinking bond comprises a crosslink that results from carbon-carbon double bond or carbon-carbon triple bond polymerization.

In preferred examples, the functional group-containing polymer is polyacrylic acid and the crosslinking agent is alkylene diamine.

Preferably, examples of the electron-releasing group include at least one group selected from the group consisting of —OR, —$OCH_2R$, —$OCOCH_2R$, —NHR, —$N(CH_2R)_2$, —$NHCOCH_2R$, —$CH_2R$, and —$C_6H_4R$, where R is hydrogen, a substituted hydrocarbon group, or an unsubstituted hydrogen group. In addition, preferably, examples of the semiconductor nanoparticle surface-coating compound include one or more compounds selected from the group consisting of primary amines ($R_1NH_2$), secondary amines ($R_1R_2NH$), tertiary amines ($R_1R_2R_3N$), and quaternary ammonium compounds ($R_4R_5R_6R_7N^+$), where $R_1$ to $R_7$ are each hydrogen, a substituted hydrocarbon group, or an unsubstituted hydrogen group and $R_1$ to $R_7$ preferably comprise a substituent at a terminal opposite to an amino group or ammonium group.

Preferably, specific examples of the semiconductor nanoparticle material include, but are not limited to, one or more materials selected from the group consisting of ZnO, ZnS, ZnSe, ZnTe, CdO, CdS, CdMnS, CdSe, CdMnSe, CdTe, CdMnTe, HgS, HgSe, HgTe, InP, InAs, InSb, InN, GaN, GaP, GaAs, GaSb, $TiO_2$, $WO_3$, PbS, PbSe, MgTe, AlAs, AlP, AlSb, AlS, Ge, and Si. In addition, a semiconductor nanoparticle having a multilayer structure consisting of a core portion and a shell portion may be made of one or more member of the aforementioned group.

The particle size of the semiconductor nanoparticle of the present invention exhibits a deviation of less than 10% rms in diameter, thereby achieving monodispersion.

Moreover, the semiconductor nanoparticle of the present invention is characterized in that it emits light in a narrow spectrum range of less than 60 nm in terms of full width at half maximum (FWHM) upon being irradiated with excitation light.

Secondly, the present invention is an invention of a method for manufacturing a semiconductor nanoparticle, which comprises a process for arranging electron-releasing groups on the surface of a semiconductor nanoparticle by adding surface-treating material that provides one or more electron-releasing groups to the semiconductor nanoparticle, a process for coating the surface of said semiconductor nanoparticle, on which the electron-releasing groups are arranged, with compounds a process for allowing a functional group-containing polymer to electrostatically bind to the surface of said semiconductor nanoparticle, and a process for causing functional groups of the functional group-containing polymer to form a crosslink via a crosslinking agent.

As above, preferably, examples of functional groups of the functional group-containing polymer include, but are not limited to, one or more groups selected from the group consisting of —COOH, —OH, —$NH_2$, —SH, —OCN, —CNO, —CHO—CH=O, —CH=$CH_2$, and —C≡CH.

Preferably, examples of the crosslinking reaction include one or more reactions selected from the group consisting of an esterification reaction, an amidation reaction, an imidation reaction, an etherification reaction, an urethanation reaction, a sulfidation reaction, a polysulfidation reaction, a carbonate reaction, a thiolation reaction, a thioesterification reaction, and a thiourethanation reaction. A carbon-carbon double bond or carbon-carbon triple bond polymerization reaction is also effective for the formation of an organic layer as an outer shell of the semiconductor nanoparticle.

Particularly, in preferred examples, the functional group-containing polymer is polyacrylic acid and the crosslinking agent is alkylene diamine. Specifically, a semiconductor nanoparticle having further improved durability and a surface condition that is particularly preferable for bio-related applications is obtained by allowing a polymer such as polyacrylic acid to electrostatically bind to the surface of a semiconductor nanoparticle that has been coated with organic compounds or by surface reforming with the use of electric charges on the surface of the semiconductor nanoparticle, and further by allowing the polymer to form a crosslinking bond with another polymer with the use of ethylenediamine, 1-ethyl-3-(3-dimethylaminopropyl)carbodiimide (EDC), or the like.

Preferably, examples of a surface-treating material that provides electron-releasing groups to a semiconductor nanoparticle surface include at least a pure metal, a metal compound, nitrogenated compounds selected from the group consisting of ammonia, amines, ammoniums, nitriles, and isocyanates, or oxygenated compounds selected from the group consisting of alcohols, phenols, ketones, aldehydes, carboxylic acids, esters of organic or inorganic acids, ethers, acid amides, and acid anhydrides.

Preferably, examples of the semiconductor nanoparticle-coating material include at least one material selected from the group consisting of primary amines ($R_1NH_2$), secondary amines ($R_1R_2NH$), tertiary amines ($R_1R_2R_3N$), and quaternary ammonium compounds ($R_4R_5R_6R_7N^+$), where $R_1$ to $R_7$ are each hydrogen, a substituted hydrocarbon group, or an unsubstituted hydrocarbon group, and $R_1$ to $R_7$ preferably comprise a substituent at a terminal opposite to an amino group or ammonium group.

Thirdly, the present invention is an invention regarding semiconductor nanoparticle applications, and the invention relates to a fluorescent reagent and an optical device.

According to the present invention, semiconductor nanoparticles that are available for use in industries related to bio-applications can be synthesized. Further, reagents that are relatively safer than those used in existing methods can be used, so that a synthesis method that is performed under safe reaction conditions can be selected. Thus, semiconductor nanoparticles that are suitable for mass synthesis and the like can be produced in a more industrially adequate manner.

DESCRIPTION OF THE PREFERRED EMBODIMENTS

Figure 1:
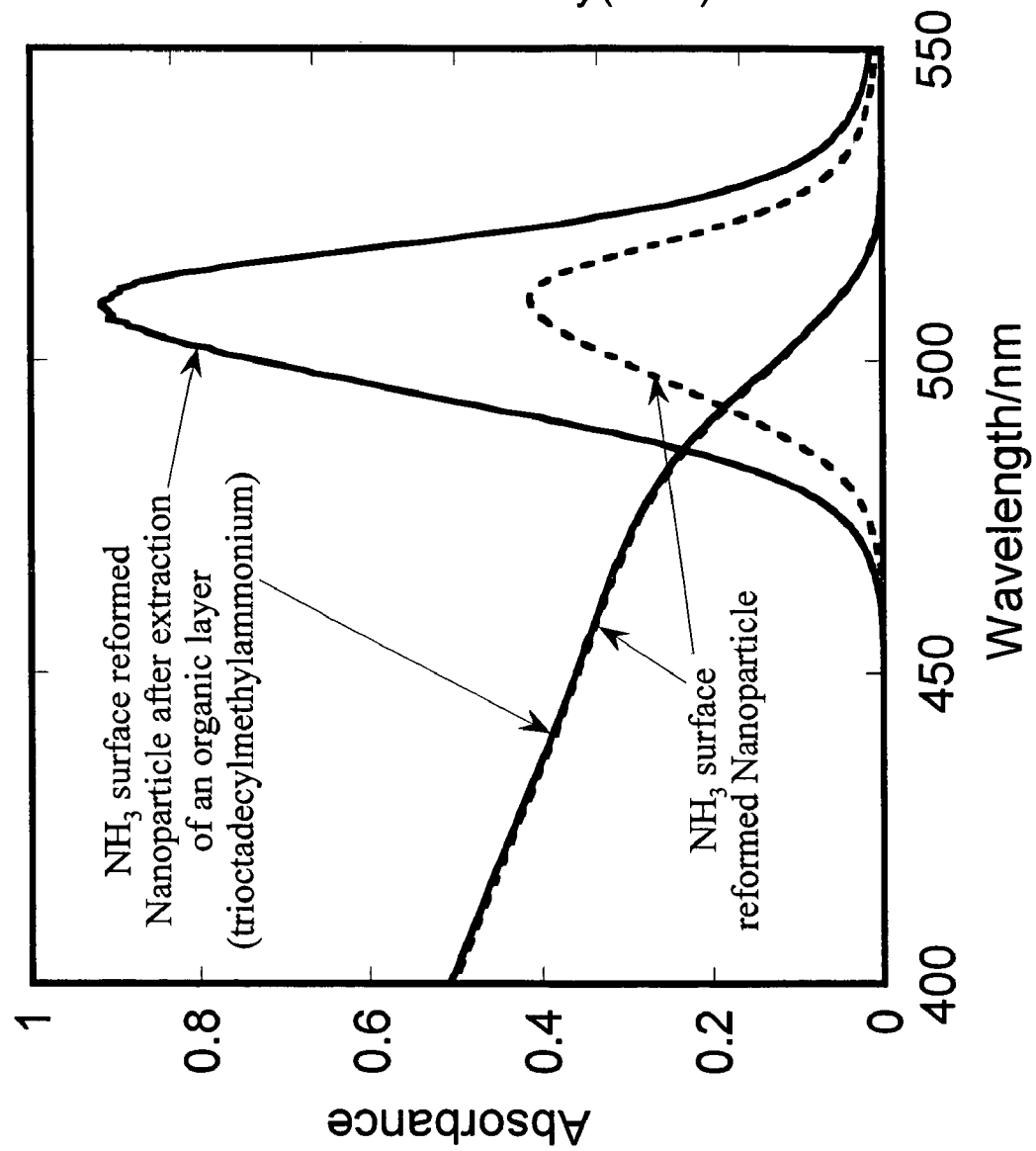
FIG. 1 shows optical spectra and emission intensities of a $NH_3$ surface reformed semiconductor nanoparticle and a semiconductor nanoparticle obtained by adding an ammonium compound to an aqueous solution containing the surface reformed semiconductor nanoparticle.

The preferred embodiments for carrying out the present invention will be described below.

EXAMPLES (In the Case of Using a Size Selective Photoetching Technique)

First, 61.8 mg of sodium hexametaphosphate (0.1 mmol) and 84.4 mg of cadmium perchlorate (0.2 mmol) were added to a container filled with 1000 ml of 30° C. ultrapure water, 141.960 mg of disodium hydrogenphosphate (1 mmol) was added thereto, and then this solution was stirred for 30 minutes in a container that was sealed while nitrogen was bubbled thereinto. After that, 4.96 $cm^{-3}$ (1 atm, 25° C.) of hydrogen sulfide gas was added to the aforementioned container to result in equal amounts of $S^{2-}$ and $Cd^{2+}$ while the container was strongly shaken, and the solution was agitated for several hours at room temperature. At this time, the color of the solution changed from optically clear colorless to optically clear yellow. Moreover, after removing unreacted hydrogen sulfide in the solution by bubbling nitrogen into the solution, oxygen bubbling was carried out for 10 minutes and 25.7 mg of methyl viologen (0.1 mmol) was added to the solution. Here, the aforementioned solution was irradiated with monochromatic light using a laser, etc. or light from a mercury vapor lamp that had passed through a filter to control the particle size using a size selective photoetching technique. Then, after the aforementioned solution was agitated for 30 minutes while nitrogen was bubbled into the solution, 50 μl of 3-mercaptopropionic acid was added thereto and the resultant was agitated for one night under shading.

(In the Case of Not Using a Size Selective Photoetching Technique)

First, 61.8 mg of sodium hexametaphosphate (0.1 mmol) and 84.4 mg of cadmium perchlorate (0.2 mmol) were added to a container filled with 1000 ml of 30° C. ultrapure water, 28.392 mg of disodium hydrogenphosphate (0.2 mmol) and 95.984 mg of sodium dihydrogenphosphate (0.8 mmol) were added thereto, and then this solution was stirred for 30 minutes in a container that was sealed up while nitrogen was bubbled thereinto. After that, 4.96 $cm^{-3}$ (1 atm, 25° C.) of hydrogen sulfide gas was added to the aforementioned container to result in equal amounts of $S^{2-}$ and $Cd^{2+}$ while the container was strongly shaken, and the solution was agitated for several hours at room temperature. Moreover, after removing unreacted hydrogen sulfide in the solution by bubbling nitrogen into the solution, 50 μl of 3-mercaptopropionic acid was added to the solution, followed by agitation for one night under shading.

1000 ml of solution prepared by either method described above was ultra-filtered and concentrated to several milliliters so as to remove methyl viologen, hexametaphosphoric acid, unreacted thiol compound, and ions, etc. dissolved upon photoetching from the aqueous solution, such that a solution containing semiconductor nanoparticles having surfaces modified with a pure thiol compound was prepared. Then, it was ultra-filtered by adding pure water and refined by repeating this process several times. Thereafter, a surface reforming treatment was performed by using the solution, which was finally concentrated to several milliliters.

The refined thiol-modified semiconductor nanoparticle solution obtained as described above was diluted by using 0.1M $NH_3$ aq. so as to have an absorbance of 0.5, and surface treatment was carried out by allowing it stand for several days under irradiating fluorescent light. Accordingly, a semiconductor nanoparticle solution having high luminescence properties was obtained. The obtained solution was optically clear yellow and it had excellent luminescence properties. Optical spectra from such time are shown in FIG. 1.

A mixed solution made by adding tridodecylmethylammonium chloride to an organic solvent such as hexane to a concentration of 1 mg/ml with respect to the solvent was added to the aforementioned surface reformed semiconductor nanoparticle solution in an amount such that it accounted for 1/10 of the amount of the solution. Or, alternatively, a mixed solution made by adding trioctadecylmethylammonium bromide to an organic solvent to a concentration of 2 mg/ml with respect to the solvent was added to the surface reformed semiconductor nanoparticle solution in an amount such that it accounted for 1/10 of the amount of the solution, and methanol was added thereto in an amount such that it accounted for 1/5 of the amount of the solution. Either one of these resulting solutions was strongly agitated for a certain time. As a result, it could be confirmed that the optically clear yellow part was transferred from the aqueous phase to the organic phase. Then, after performing a centrifugal separation, the aqueous phase and the organic phase were separated. The aforementioned recovered organic phase was diluted by adding an organic solvent such as hexane so as to result in the same absorbance as that of the aforementioned aqueous solution before transfer. The semiconductor nanoparticles transferred to the organic phase still maintained high luminescence properties. Optical spectra from such time are shown in FIG. 1.

Figure 2:
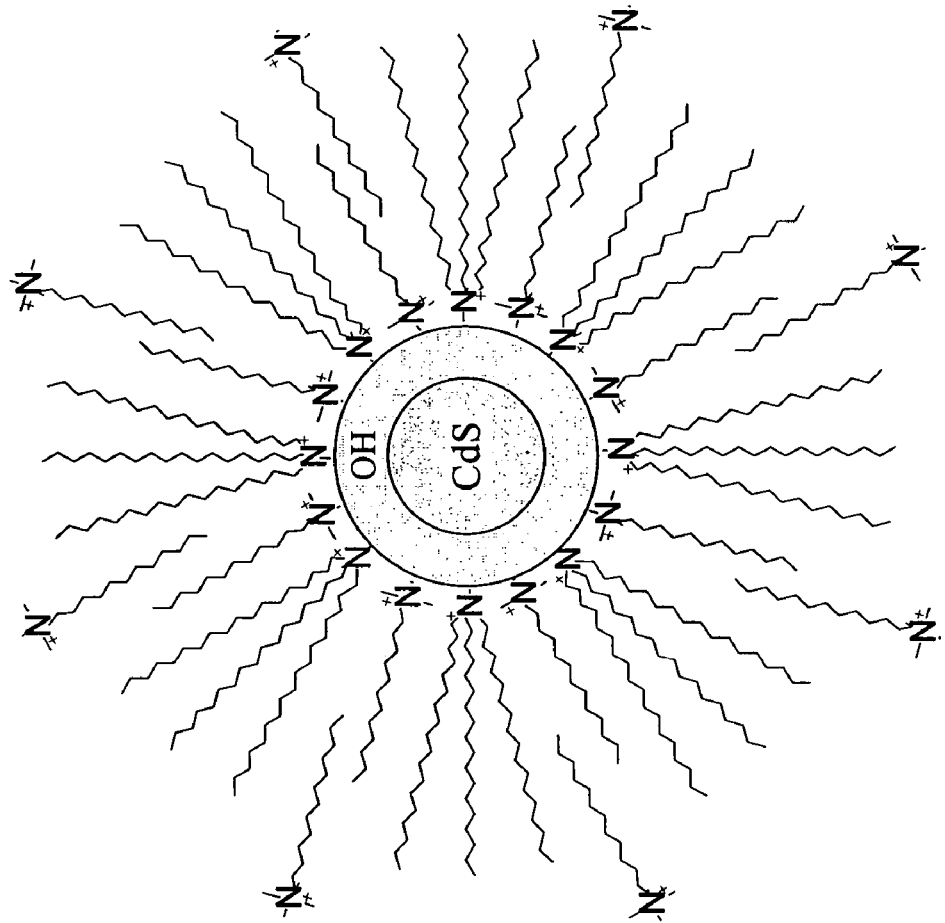
FIG. 2 shows a schematic diagram of a semiconductor nanoparticle obtained by adding an ammonium compound to a $NH_3$ surface reformed semiconductor nanoparticle.
Figure 3:
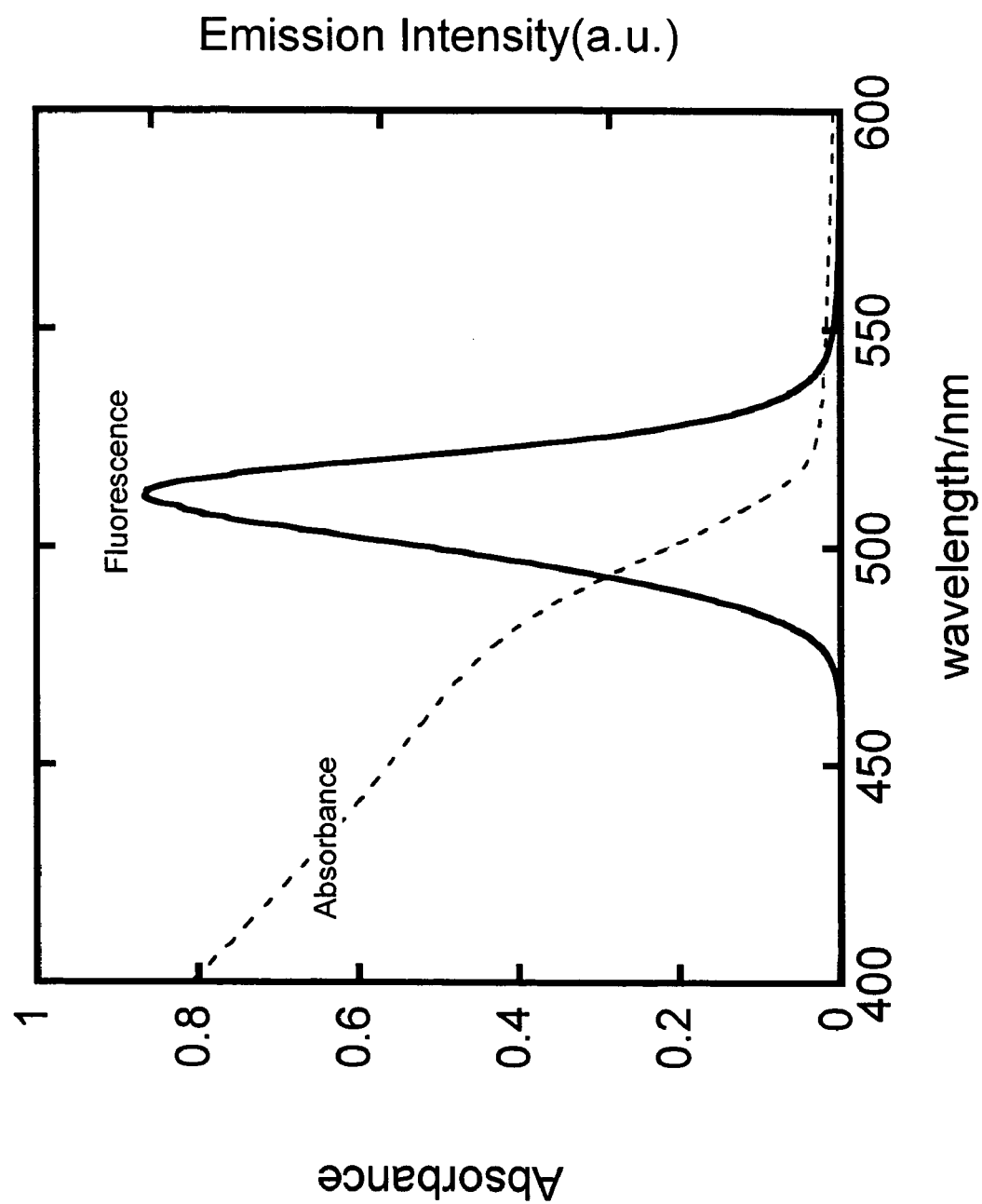
FIG. 3 shows optical spectra and emission intensities of a semiconductor nanoparticle obtained by adding an ammonium compound to a $NH_3$ surface reformed semiconductor nanoparticle.

Nanoparticles perfectly dispersed into the organic solvent obtained as mentioned above were coated with amphipathic molecules. 10 ml of a solution in which nanoparticles had perfectly dispersed into the aforementioned organic solvent was put into a container such as a stoppered test tube or an eggplant shaped flask, etc. and was made to assume a membranous form on the inner wall of the container by evaporation. Then, the particles were dissolved again by adding 2 ml of solution in which dodecyltrimethylammonium chloride was dissolved in chloroform to a concentration of 5 mM, and the resulting solution was made to assume a membranous form again on the inner wall of the container by evaporation. Moreover, after removing residual chloroform by heating the container at 90° C., the particles were dissolved again by adding 2 ml of methanol. Then, methanol was removed by adding 10 ml of ultrapure water, followed by agitation for some time during heating to 90° C. Finally, an optically clear yellow solution could be obtained by performing centrifugal separation so as to remove the precipitation. A schematic drawing and optical spectra at this time are shown in FIGS. 2 and 3, respectively.

Figure 4:
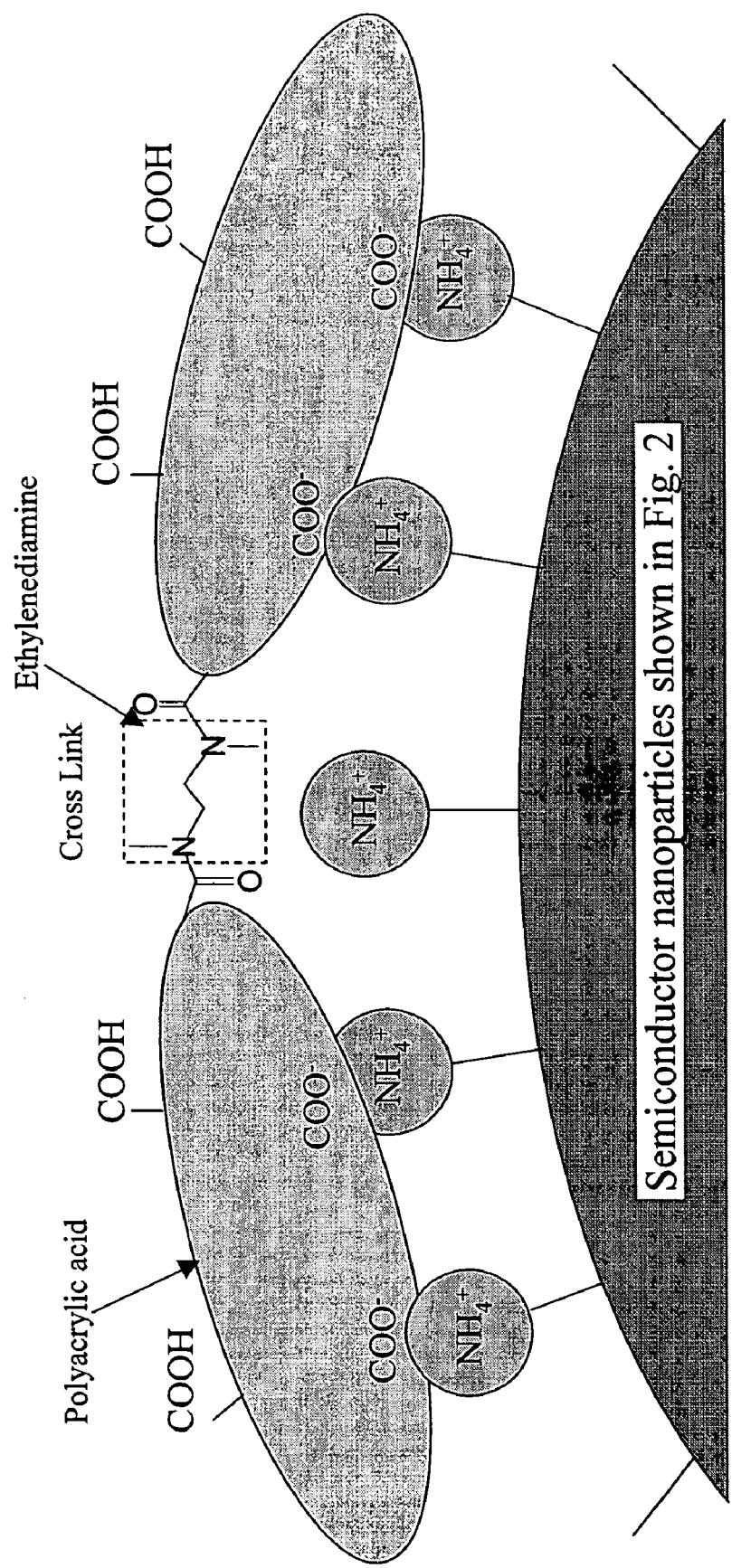
FIG. 4 shows a schematic drawing of semiconductor nanoparticles comprising a crosslink formed with polyacrylic acid and ethylenediamine.
Figure 5:
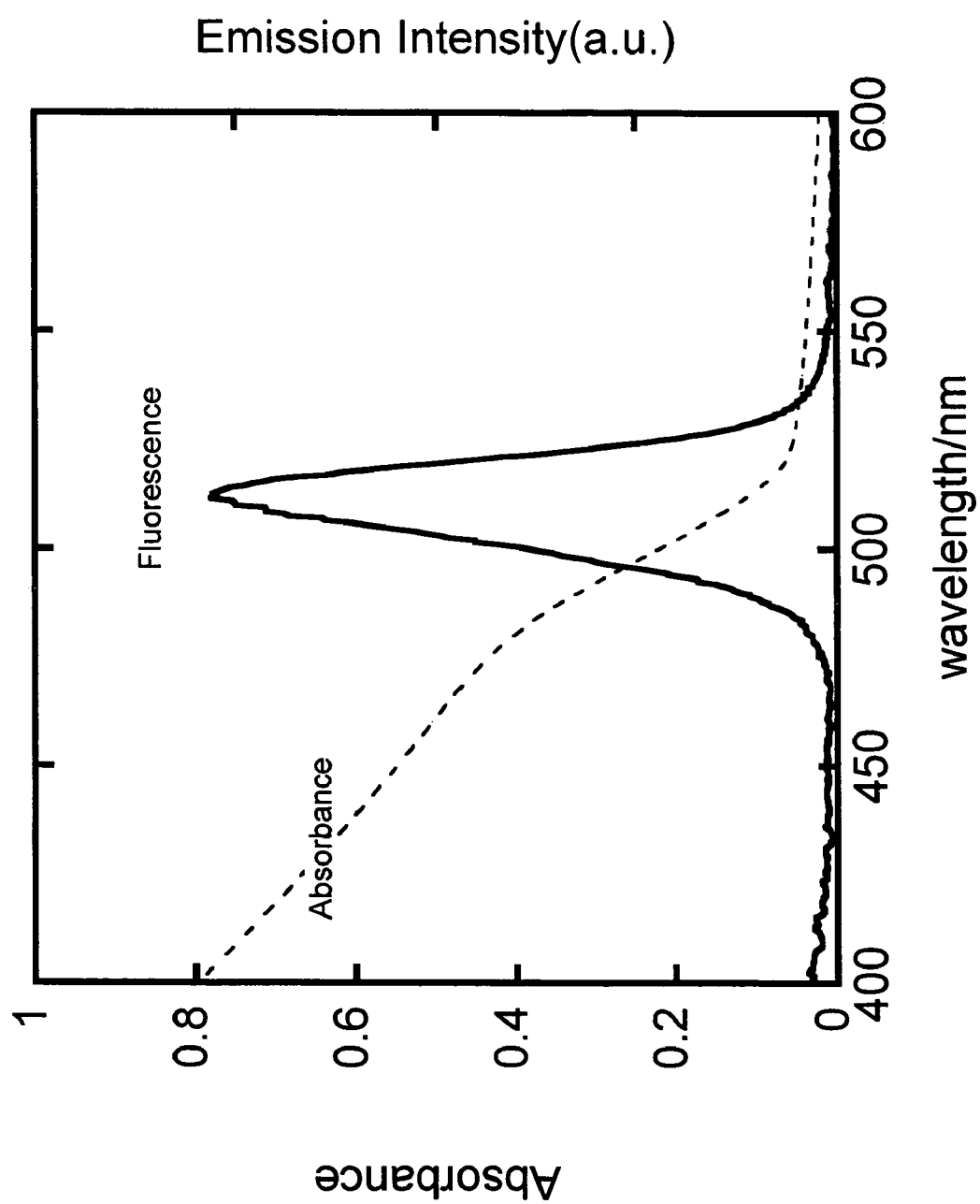
FIG. 5 shows optical spectra and emission intensities of a semiconductor nanoparticle comprising a crosslink formed with polyacrylic acid and ethylenediamine.
Figure 6:
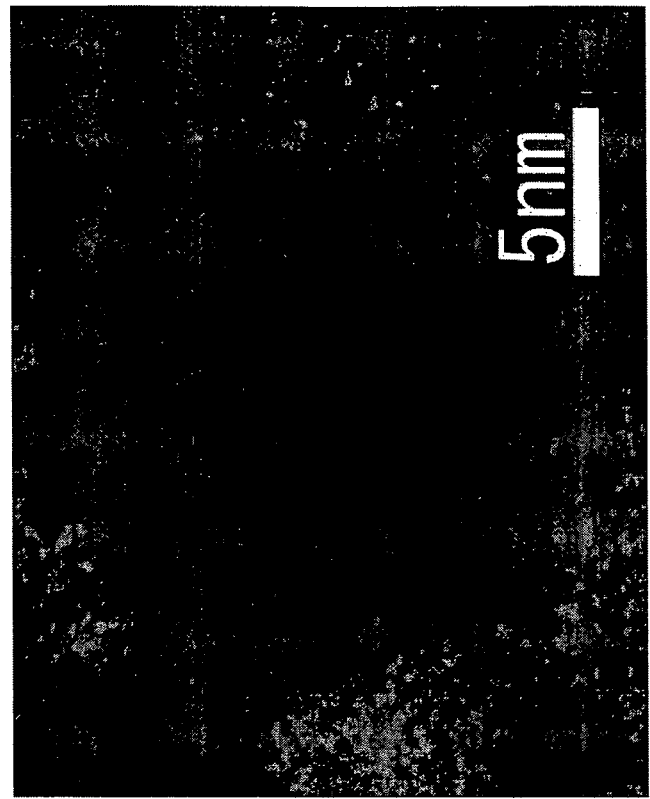
FIG. 6 shows transmission electron microscope (TEM) pictures of a semiconductor nanoparticle comprising a crosslink formed with polyacrylic acid and ethylenediamine.
Figure 6:
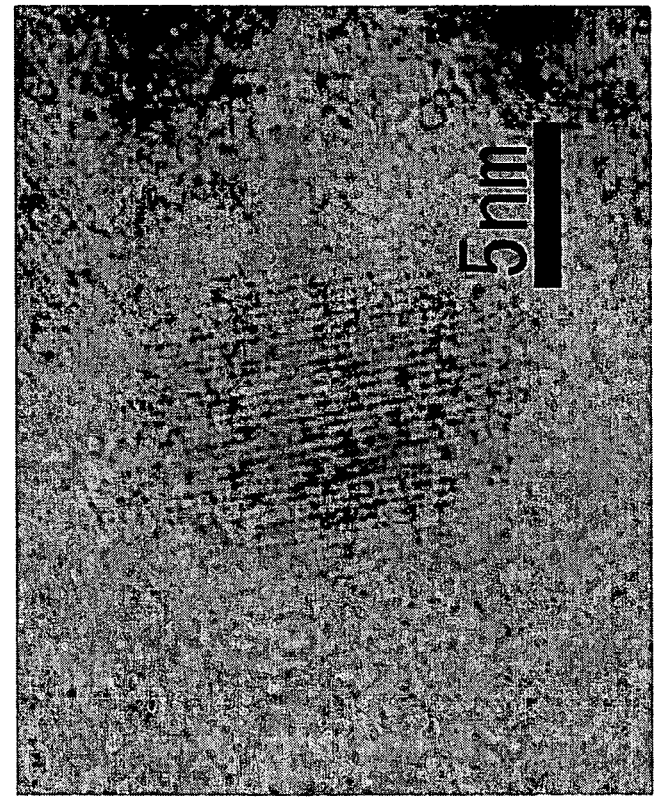

Polyacrylic acid (average molecular weight: 5000) and ethylenediamine were added to the obtained optically clear yellow solution to concentrations of 0.1 mM and 1.5 mM therein, respectively, followed by agitation for some time. Further, hydrochloric acid 1-ethyl-3-(3-dimethylaminopropyl)carbodiimide was added thereto to a concentration of 10 mM therein, followed by agitation for several days. Thereafter, the resultant was ultra-filtered so as to be refined. A schematic drawing, optical spectra, and transmission electron microscope (TEM) pictures from such time are shown in FIGS. 4, 5, and 6, respectively.

Each of the obtained nanoparticles has a carboxyl group exposed on the surface thereof. Such configuration is preferable for staining and labeling of biopolymers.

With the use of the method of the present invention, semiconductor particles having an entirely positively charged surface condition and those having a negatively charged surface condition can alternately be laminated on each other, so that the improvement of durability of the particles can be attempted. In addition, crosslinking using ethylenediamine was carried out in the Examples, while polymers used may contain a portion capable of being crosslinked. Further, in the present invention, particle size control is not particularly carried out. It is also possible to obtain fine particle sizes using an ultrasonic homogenizer, etc.; however, any particle size can be appropriate.

In addition, material that provides electron-releasing groups on the surface of a semiconductor nanoparticle may be the aforementioned material that coats a semiconductor nanoparticle or the aforementioned polymer. That is, there may be no difference between a process for arranging electron-releasing groups on the surface of a semiconductor nanoparticle by adding surface-treating material that provides one or more electron-releasing groups to the semiconductor nanoparticle and a process for coating the surface of the semiconductor nanoparticle comprising the arrangement of electron-releasing groups on such surface with compounds.

According to the present invention, it becomes possible to easily synthesize semiconductor nanoparticles that have high luminescence properties and excellent chemical stability. The semiconductor nanoparticles of the present invention can be used for fluorescent reagents and optical devices, etc. by utilizing such high luminescence properties.

What is claimed is:

1. A semiconductor nanoparticle with electron-releasing groups arranged on the surface thereof, which is modified with a functional group-containing polymer that electrostatically binds to the surface of said semiconductor nanoparticle.

2. The semiconductor nanoparticle according to claim 1, wherein said functional group-containing polymer forms a crosslinking bond via a crosslinking agent.

3. The semiconductor nanoparticle according to claim 1, wherein said functional group-containing polymer binds to the surface of the semiconductor nanoparticle via a semiconductor nanoparticle-coating compound.

4. The semiconductor nanoparticle according to claim 1, comprising said functional group-containing polymer whose functional group is one or more functional groups selected from the group consisting of —COOH, —OH, —NH$_2$, —SH, —OCN, —CNO, —CHO, —CH=O, —CH=CH$_2$, and C≡CH.

5. The semiconductor nanoparticle according to claim 2, wherein said crosslinking bond is one or more bonds selected from the group consisting of an ester bond, an amide bond, an imide bond, an ether bond, a urethane bond, a sulfide bond, a polysulfide bond, a carbonate bond, a thiol bond, a thioester bond, and a thiourethane bond.

6. The semiconductor nanoparticle according to claim 2, wherein said crosslinking bond results from carbon-carbon double bond or carbon-carbon triple bond polymerization.

7. The semiconductor nanoparticle according to claim 2, wherein said functional group-containing polymer is polyacrylic acid and said crosslinking agent is alkylene diamine.

8. The semiconductor nanoparticle according to claim 1, wherein said electron-releasing group is at least one electron-releasing group selected from the group consisting of —OR, —OCH$_2$R, —OCOCH$_2$R, —NHR, —N(CH$_2$R)$_2$, —NHCOCH$_2$R, —CH$_2$R, and —C$_6$H$_4$R, where R is hydrogen, a substituted hydrocarbon group, or an unsubstituted hydrocarbon group.

9. The semiconductor nanoparticle according to claim 3, wherein said semiconductor nanoparticle surface-coating compound is one or more compounds selected from the group consisting of primary amines (R$_1$NH$_2$), secondary amines (R$_1$R$_2$NH), tertiary amines (R$_1$R$_2$R$_3$N), and quatemary ammonium compounds (R$_4$R$_5$R$_6$R$_7$N$^+$), where R$_1$ to R$_7$ are each hydrogen, a substituted hydrocarbon group, or an unsubstituted hydrocarbon group.

10. The semiconductor nanoparticle according to claim 9, wherein R$_1$ to R$_7$ comprise a substituent at a terminal opposite to an amino group or ammonium group.

11. The semiconductor nanoparticle according to claim 1, comprising a semiconductor nanoparticle whose material is one or more materials selected from the group consisting of ZnO, ZnS, ZnSe, ZnTe, CdO, CdS, CdMnS, GdSe, CdMnSe, CdTe, CdMnTe, HgS, HgSe, HgTe, IniP, InAs, InSb, InN, GaN, GaP, GaAs, GaSb, TiO$_2$, WO$_3$, PbS, PbSe, MgTe, AlAs, AlP, AlSb, AlS, Ge, and Si, or a semiconductor nanoparticle having a multilayer structure consisting of a core portion and a shell portion that are made of one or more members of said group.

12. The semiconductor nanoparticle according to claim 1, wherein the particle size of said nanoparticle exhibits a deviation of less than 10% rms in diameter, thereby achieving monodispersion.

13. The semiconductor nanoparticle according to claim 1, wherein said nanoparticle emits light in a narrow spectrum range of less than 60 nm in terms of full width at half maximum (FWHM) upon being irradiated with excitation light.

14. A method of manufacturing a semiconductor nanoparticle comprising:
   a process for arranging electron-releasing groups on the surface of a semiconductor nanoparticle by adding surface-treating material that provides one or more electron-releasing groups to said semiconductor nanoparticle;
   a process for allowing a functional group-containing polymer to electrostatically bind to the surface of said semiconductor nanoparticle; and a process for causing functional groups of said polymer to form a crosslink via a crosslinking agent.

15. The method of manufacturing a semiconductor nanoparticle according to claim 14, comprising a process for coating said semiconductor nanoparticle, on which the electron-releasing groups are arranged.

16. The method of manufacturing a semiconductor nanoparticle according to claim 14, comprising said functional group-containing polymer whose functional group is one or more functional groups selected from the group consisting of —COOH, —OH, —NH$_2$, —SH, —OCN, —CNO, —CHO, —CH═O, —CH═CH$_2$, and —C≡CH.

17. The method of manufacturing a semiconductor nanoparticle according to claim 14, wherein said crosslink is formed by one or more reactions selected from the group consisting of an esterification reaction, an amidation reaction, an imidation reaction, an etherification reaction, a urethanation reaction, a sulfidation reaction, a polysulfidation reaction, a carbonate reaction, a thiolation reaction, a thioesterification reaction, and a thiourethanation reaction.

18. The method of manufacturing a semiconductor nanoparticle according to claim 14, wherein said crosslink is formed by a carbon-carbon double bond or carbon-carbon triple bond polymerization reaction.

19. The method of manufacturing a semiconductor nanoparticle according to claim 14, wherein said functional group-containing polymer is polyacrylic acid and said crosslinking agent is alkylene diamine.

20. The method of manufacturing a semiconductor nanoparticle according to claim 14, wherein said surface-treating material that provides electron-releasing groups to the semiconductor nanoparticle is at least a pure metal, and a metal compound, nitrogenated compounds selected from the group consisting of ammonia, amines, ammoniums, nitriles, and isocyanates, or oxygenated compounds selected from the group consisting of alcohols, phenols, ketones, aldehydes, carboxylic acids, esters of organic or inorganic acids, ethers, acid amides, and acid anhydrides.

21. The method of manufacturing a semiconductor nanoparticle according to claim 14, wherein said semiconductor nanoparticle-coating material is at least one material selected from the group consisting of primary amines (R$_1$NH$_2$), secondary amines (R$_1$R$_2$NH), tertiary amines (R$_1$R$_2$R$_3$N), and quaternary ammonium compounds (R$_4$R$_5$R$_6$R$_7$N$^+$), where R$_1$ to R$_7$ are each hydrogen, a substituted hydrocarbon group or an unsubstituted hydrocarbon group.

22. The method of manufacturing a semiconductor nanoparticle according to claim 21, wherein R$_1$ to R$_7$ comprise a substituent at a terminal opposite to an amino group or ammonium group.

23. The method of manufacturing a semiconductor nanoparticle according to claim 14, comprising a semiconductor nanoparticle whose material is one or more materials selected from the group consisting of ZnO, ZnS, ZnSe, ZnTe, CdO, CdS, CdMnS, CdSe, CdMnSe, CdTe, CdMnTe, HgS, HgSe, HgTe, InP, InAs, InSb, InN, GaN, GaP, GaAs, GaSb, TiO$_2$, WO$_3$, PbS, PbSe, MgTe, AlAs, AlP, AlSb, AlS, Ge, and Si, or a semiconductor nanoparticle having a multilayer structure consisting of a core portion and a shell portion that are made of one or more members of said group.

24. A fluorescent reagent comprising the semiconductor nanoparticle with electron-releasing groups arranged on the surface thereof, which is modified with a functional group-containing polymer that electrostatically binds to the surface of said semiconductor nanoparticle.

25. An optical device comprising the semiconductor nanoparticle with electron-releasing groups arranged on the surface thereof, which is modified with a functional group-containing polymer that electrostatically binds to the surface of said semiconductor nanoparticle.

* * * * *